United States Patent [19]

Stein

[11] 4,151,293
[45] Apr. 24, 1979

[54] INSECTICIDAL PYRAZOLE-4-METHANOL ESTERS

[75] Inventor: Robert G. Stein, Kenosha, Wis.

[73] Assignee: Abbott Laboratories, North Chicago, Ill.

[21] Appl. No.: 953,714

[22] Filed: Oct. 23, 1978

[51] Int. Cl.² ............... A61K 31/415; C07D 231/12
[52] U.S. Cl. .................................. 424/273 P; 548/378
[58] Field of Search ................... 548/378; 424/273 P

[56] References Cited

U.S. PATENT DOCUMENTS

| | | | |
|---|---|---|---|
| 3,666,756 | 5/1972 | Fukumura et al. | 548/378 |
| 3,702,333 | 11/1972 | Nakanishi et al. | 424/285 |
| 3,835,220 | 9/1974 | Matsui et al. | 424/285 |
| 3,857,863 | 12/1974 | Ohno et al. | 424/285 |
| 3,862,174 | 1/1975 | Mizutami et al. | 424/285 |
| 3,996,244 | 12/1976 | Fujimoto et al. | 424/285 |
| 3,998,868 | 12/1976 | Mizutami et al. | 424/285 |
| 4,083,989 | 4/1978 | Kohn | 548/378 |

Primary Examiner—John M. Ford
Assistant Examiner—Natalia Harkaway
Attorney, Agent, or Firm—Paul D. Burgauer; Robert L. Niblack

[57] ABSTRACT

Compounds of the formula

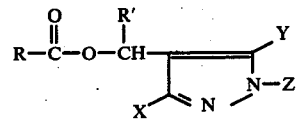

wherein R is phenyl, benzyl, 1-isopropylbenzyl wherein each of said aromatic rings may carry a chlorine substituent,

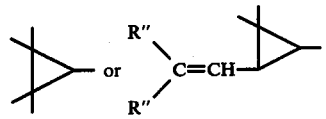

R' is H, —C≡N or —C≡CH; R" is chlorine, bromine, fluorine or methyl; X and Y both but independently are H or loweralkyl; and Z is phenyl or benzyl which may carry an optional aromatic chlorine substituent, have been found to be excellent insecticides, ovicides and/or miticides.

17 Claims, No Drawings

INSECTICIDAL PYRAZOLE-4-METHANOL ESTERS

DETAILED DESCRIPTION OF THE INVENTION

This invention is directed to compound of the formula

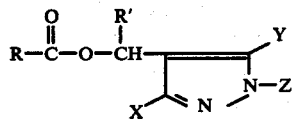

wherein R is phenyl, benzyl, 1-isopropylbenzyl wherein each of said aromatic rings may carry a chlorine substituent,

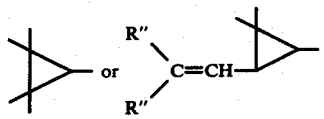

R' is H, —C≡N or —C≡CH;
R" is chlorine, bromine, fluorine or methyl; X and Y both but independently are H or loweralkyl; and and Z is phenyl or benzyl which may carry an optional aromatic chlorine substituent. These compounds have been found to protect agricultural crops against mites or insects of various types. These compounds are also useful to combat common houseflies and their eggs in a nonagricultural setting.

In a general embodiment, the compounds of the above formula are made by a simple esterification process using approximately equimolar amounts of RCOOH and the appropriately substituted HO—CH-R'—pyrazole wherein R', X, Y and Z have the above meaning, in the presence of an inert diluent. Of course, the esterification is preferably carried out with a more active derivative of RCOOH such as the acid chloride or the anhydride. In the case of using ROCl, it will be obvious to the skilled artisan to use an acid acceptor in the esterification mixture. The required pyrazolylmethanol can be prepared by a Vilsmeier-Haack raction from the known N-benzylpyrazole carrying optional substituents X and Y to its carboxyaldehyde with POCl$_3$ and DMF, reducing the formed carboxyaldehyde with sodium borohydride and, if desired, introducing substituent R'.

Detailed procedures for making the compounds of the present invention will be seen from the following examples which, however, serve only as illustrations and are not intended to limit the invention in any respect.

EXAMPLE 1

1-(1-Benzyl-4-pyrazolyl)-1-cyanomethyl ester of chrysanthemic acid (a) To 10.2 g. of dimethylformamide in an ice bath was added 5.4 g. of phosphorous oxychloride under stirring. Stirring was continued for 1 hour at which time the ice bath was removed and 4.8 g. of 1-benzyl-pyrazole (prepared according to Jones, JACS 71, 3994 ff of 1949) was added rapidly. The mixture was stirred 3 hours at 85 degrees C., and after cooling, the dark solution was poured into 50 ml. of water. The solution was adjusted to pH 8 by adding 50% aqueous NaOH and was then extracted with ether. The combined extracts were washed with water, dried over magnesium sulfate, filtered and evaporated in vacuo to produce 3.8 g. of an oil, b. 142–4 degrees C./0.5 mm, identified as 1-benzyl-pyrazole-4-carboxyaldehyde.

(b) To a stirred solution of the described product in 75 ml. of methanol was added 2.6 g. of sodium borohydride. After the addition, the mixture was heated for 1 hour on a steam bath, followed by concentration in vacuo. After adding 25 ml. of water to the residue, this mixture was extracted with ether and the extract was worked up as in (a) to yield 3.5 g. of 1-benzyl-4-hydroxymethyl-pyrazole, b. 142–5 degrees C./0.2 mm.

(c) A solution of 28.8 g. of potassium cyanide in 150 ml. of glacial acetic acid was added dropwise to a solution of 18.6 g. of the product from (b) above in 90 ml. of ethanol in an ice bath. The mixture was stirred and allowed to adjust to room temperature in 24 hours before it was poured into 500 ml. of water. The separating oil was extracted with ether and the extract was washed with an aqueous sodium bicarbonate solution until it became alkaline, then with 75 ml. of an aqueous saturated sodium bisulfite solution, and finally with 75 ml. of water. Further work-up as in (a) yielded 21.28 g. of the described 1-benzyl-4-cyanohydroxymethyl-pyrazole.

(d) To a solution of 3.1 g. of chrysanthemic carboxylic acid in 15 ml. of benzene was added 2.4 g. of thionyl chloride and the mixture was refluxed for 2 hours. After subsequent removal of the excess thionyl chloride, more benzene was added and then removed under reduced pressure. The residue was taken up in 15 ml. of benzene and added dropwise to a magnetically stirred solution of 3.9 g. of the product of (c) above in 15 ml. of benzene. The mixture was stirred and refluxed for 18 hours and cooled to room temperature. After adding 15 ml. of water, the precipitated triethylamine hydrochloride dissolved. the organic layer was separated in the usual fashion and distilled, producing 5.6 g. of the desired 1-(1-benzyl-4-pyrazolyl)-1-cyanomethyl ester of chrysanthemum acid.

When the above 1-benzylpyrazole is made in accordance with the Jones reference but starting with the 3-methyl- or the 3,5-dimethyl-pyrazole, the above procedure leads to the corresponding compounds of formula I wherein X and Y are methyl.

EXAMPLE 2

1-Benzyl-4-pyrazolylmethyl ester of 3-(2,2-dichloroethenyl)-2,2-dimethylcyclopropyl carboxylic acid By condensing the 1.98 g. of the product of Example 1 (b) with 2.2 g. of 3-(2,2-dichloroethenyl)-2,2-dimethylcyclopropylcarboxylic acid in accordance with Example 1 (d), the desired 1-benzyl-4-pyrazolylmethyl ester of 3-(2,2-dichloroethenyl)-2,2-dimethylcyclopropylcarboxylic acid is obtained. The crude product was chromotographed from a chloroform solution over 75 g. of Florisil of 100–200 mesh size to produce 3.83 g. of the pure compound.

By replacing the above 2,2-dichloroethenyl-compound with 3.0 g. of the corresponding 2,2-dibromoethenyl (Brown et al; J. Agr. Food Chem., 21 No. 5 p. 757 of 1973) or 1.7 g. of the corresponding 2,2-difluoroethenyl analog (Brown et al; J. Agr. Food Chem. 23 No. 1, p. 115 of 1975), one obtains the 1-benzyl-4-pyrazolylmethenyl ester of 3-(2,2-dibromoethenyl)-2,2-dimethylcyclopropyl or the same ester of 3-(2,2- difluoroethenyl)-2,2-dimethylcyclopropyl, respectively, in corresponding yields.

EXAMPLE 3

1-(1-Benzyl-4-pyrazolyl)-1-propargyl ester of 3-(2,2-dichloroethenyl)-2,2-dimethylcyclopropylcarboxylic acid To 60 ml. of dry dioxane saturated with acetylene and magnetically stirred, was added 5.5 g. of lithium acetylide ethylene diamine complex, followed by the dropwise addition of a solution of 9.3 g. of the product of Example 1 (a) in 50 ml. of dry dioxane over a period of 30 minutes. During this addition and subsequent 30 minutes, dry acetylene was bubbled through the stirred mixture. This was followed by stirring for 18 hours under nitrogen. A solution of 13.4 g. of ammonium chloride in 30 ml. of water was dropwise added to this mixture, dissolving all formed salts. After another 60 minutes of stirring, the organic (dioxane) layer was separated, the aqueous solution was extracted with ether, and the dioxane and ether solutions were combined. Washing the extract with 50 ml. of a saturated aqueous sodium bisulfite solution and 50 ml. of water and further work-ups as in Example 1 (a) produced 5.3 g. of crude 1-(1-benzyl-4-pyrazolyl)-propargyl alcohol.

Esterification of this material with 3(2,2-dichloroethyl)-2-2-dimethylcyclopropylcarboxylic acid in accordance with Example 1 (d) and work-up as in Example 2, produced the desired ester named above.

EXAMPLE 4

1-(1-Benzyl-4-pyrazolyl)-1-cyanomethyl ester of 3-(2,2-dichloroethenyl)-2,2-dimethylcyclopropylcarboxylic acid By following the procedure of Example 1 (d) with the product of Example 1 (c) and the cyclic acid used in Example 2, and work-up according to Example 2, the above named ester is obtained.

EXAMPLE 5

1-Benzyl-4-pyrazolylmethyl ester of chrysanthemic acid

By condensing 3.1 g. of chrysanthemic carboxylic acid with 3.4 g. of the product of Example 1 (b) in accordance with Example 1 (d), an oily residue was obtained which was fractionated at 0.1 mm pressure. A yield of 4.5 g. of the desired ester was obtained after discarding lower-boiling fractions. The new ester distills at 184–7 degrees C./0.1 mm and shows $N_D^{24.5}$ 1.5374.

EXAMPLE 6

1-Benzyl-4-pyrazolylmethyl ester of tetramethylcyclopropylcarboxylic acid

Esterification of 2.8 g. of 2,2,3,3-tetramethylcyclopropylcarboxylic acid with 3.8 g. of the compound of Example 1 (b) in accordance with Example 2 produced the expected ester. The chloroform extracts of the first 225 ml. were combined to yield 6.15 g. of the desired ester.

EXAMPLE 7

1-(1-Benzyl-4-pyrazolyl)-cyanomethyl ester of tetramethylcyclopropylcarboxylic acid By condensing the alcohol of Example 1 (c) with the acid used in Example 6 by the procedure of Example 1 (d), a solid residue of the desired ester was obtained, m. 88–9 degrees C.

EXAMPLE 8

1-Benzyl-3,5-dimethyl-4-pyrazolylmethyl ester of 3-(2,2-dichloroethenyl)-2,2-dimethylcyclopropylcarboxylic acid Condensation according to Example 1 (d) with the cyclic acid used in Example 2 and 1-benzyl-3,5-dimethyl-4-hydroxymethylpyrazole produced the desired acid as an oil which was chromatographed in accordance with Example 2.

EXAMPLE 9

1-Phenyl-4-pyrazolylmethyl ester of 3-(2,2-dichloroethenyl)-2,2-dimethylcyclopropylcarboxylic acid By substituting 1-phenyl-4-hydroxymethylpyrazole for the pyrazole used in Example 8, the desired compound was obtained as an oil requiring chromatographic purification.

EXAMPLE 10

1-(p-Chlorobenzyl)-4-pyrazolylmethyl ester of 3-(2,2-dichloroethenyl)-2,2-dimethylcyclopropylcarboxylic acid By substituting p-chlorobenzyl-4-hydroxymethylpyrazole for the pyrazole in Example 8, the desired compound was obtained as an oil requiring chromatographic purification.

EXAMPLE 11

1-Benzyl-4-pyrazolylmethyl ester of 2-p-chlorophenyl-3-methylbutyric acid

By following the procedure of Example 1 (d) but with 2.1 g. of p-chlorophenyl-3-methylbutyric acid and 1.88 g. of the product of Example 1 (b), the desired ester was obtained as an oil in a yield of 4.2 g. The crude oil was distilled under reduced pressure to produce 3.0 g. of the pure ester, b. 206–9 degrees C./0.1 mm; $N_D^{25} = 1.5594$.

EXAMPLE 12

1-(1-Benzyl-4-pyrazolyl)-1-cyanomethyl ester of 2-p-chlorobenzyl-3-methylbutyric acid This compound was obtained by the esterification process of the preceding examples, using the acid of Example 11 and the alcohol of Example 1 (c). The new ester was purified by crystallization from isopropanol; m. 103–4 degrees C.

EXAMPLE 13

1-(1-Benzyl-4-pyrazolyl)-1-propargyl ester of 2-p-chlorobenzyl-3-methylbutyric acid This compound was made by the esterification of the alcohol described in Example 3 and the butyric acid derivative of Example 11 in accordance with the preceding examples. The new ester was obtained as an oil which solidified upon standing. In all the above examples, the microanalysis confirmed the expected empirical formulae of the compounds and in each instance, the nuclear magnetic resonance and infrared spectra were in conformance with the assigned structure while the thin-layer chromatograms confirmed the purity of the compounds.

EXAMPLE 14

Testing Procedure (A) Approximately fifty 3-day old adult houseflies were used for each dilution of the above compounds. Initial tests were carried out at 2500 ppm made from a stock solution of 50,000 ppm in a DMF/isopropanol 1:3 (vol.) mixture containing 4% of a commercial wetting agent; the diluent was a 70% aqueous acetone mixture.

The flies were anesthetized with $CO_2$ and placed on a Buchner funnel. The appropriate dilution was poured onto the flies and kept in contact with them for about 5 seconds. The test mixture was removed by suction and the flies transferred to a pint ice-cream container which was covered with a transparent top. Mortality was noted after 60 minutes.

Where mortality was 80–100% at 2500 ppm, the tests were repeated with 250 ppm, 100 ppm, 25 ppm, 10 ppm and 1 ppm to determine the minimum lethal dose. Activity of each dilution was rated as follows:

3 = mortality of 80–100%: marked
2 = mortality of 50–80%: moderate
1 = mortality of 25–50%: slight
0 = mortality of 25%: inactive.

(B) Approximately fifteen 4-day old cabbage looper larvae were used for each dilution of the above compounds. Initial tests were carried out at 2500 ppm made from a stock solution of 50,000 ppm in the same fashion as described under (A).

The larvae were placed in a Buchner funnel. The appropriate test solution was poured onto them and kept in contact with them for about 5 seconds. The solution was then removed by suction and the worms were placed in a petri dish along with a leaf from a Henderson Bush Lima Bean plant. Mortality was determined after 24 hours, and the procedure was repeated at lower concentrations as in (A) with the same rating scale being used.

(C) To test the effect on cuticle formation or molting process in insects, 4-day old, third instar cabbage looper larvae were used. They were reared to the test age on a meridic, alfalfa meal, casein, wheat germ diet. The initial test was carried out with the test compound at 200 ppm in acetone. Aliquots of 0.5 ml. of this solution were spread evenly over the surface of semisynthetic looper diet contained in 100×20 mm petri dishes. A microbiological turntable and a glass rod were used to insure even distribution and the solution was allowed to dry for 15 minutes. Ten 4-day old larvae were placed on the diet and incubated at 30 degrees C. Mortality was made at 2, 5 and 10 days or until pupation occurred in controls and activities were assigned as in (A).

(D) This test was designed to screen those compounds which may effect embryogenesis of insect and mite eggs. A fresh strip was taken from an appropriate cage of young adult cabbage loopers. This strip was disinfected for 10 minutes in a 10% formaldehyde solution. This step was necessary to surface sterilize the eggs to prevent extraneous mortality to newly emerged larvae from viruses and other pathogens. After treatment in the formaldehyde solution, egg strips were rinsed in running tap water for thirty minutes and then allowed to air dry. Following drying, the egg strip was cut into 1 inch squares. One square containing no less than 10 eggs was used for each test compound; the compounds are initially screened at 500 ppm. The test solution was made up and diluted as in (A).

An egg patch was placed into a Buchner funnel, attached to a vacuum source. Ten ml. aliquots of the appropriate compound were poured directly onto the patch. The chemical was immediately removed by suction. The egg patch was allowed to air dry and the number of eggs per patch was recorded. The treated eggs were then placed in a disposable petri dish (100×20 mm.) containing 30 ml. of normal looper rearing media (casein, alfalfa meal, wheat germ diet). A disc of filter paper, 11 cm in diameter, was placed over the dish. The plastic lid was then pressed over the filter paper to seal the dish, which was then incubated at 30±1 degrees C. for six days.

To evaluate activity, the number of larvae emerging from each egg patch were counted. These were compared to the number of eggs contained in the patch and percent emergence was then calculated. Active compounds at 500 ppm were retested at 250 and 125 ppm or lower concentrations to determine the minimum lethal dose with activities assigned as in (A).

All results are shown in the following table:

| Test & Concentration in ppm | | Compound of Example | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 | 13 |
| A | 500 | 3 | 3 | 3 | 3 | 3 | 2 | 3 | 3 | 3 | 3 | 3 | 1 | 3 |
|   | 250 | 2 | 3 | 3 | 3 | 2 | 1 | 3 | 3 | 2 | 3 | 3 | 0 | 3 |
|   | 125 | 1 | 3 | 3 | 3 | 1 | 1 | 3 | 3 | 1 | 3 | 2 | 1 | 3 |
|   | 63  | 0 | 3 | 3 | 3 | 0 | 0 | 0 | 3 | 1 | 2 | 0 | 1 | 2 |
|   | 31  | 0 | 2 | 3 | 2 | 0 | 0 | 0 | 2 | 0 | 1 |   |   |   |
| B | 500 | 3 | 3 | 3 | 3 | 3 | 1 | 2 | 3 |   | 3 | 3 | 1 | 3 |
|   | 250 | 3 | 3 | 3 | 3 | 2 | 2 | 2 | 3 |   | 3 | 3 | 0 | 3 |
|   | 125 | 2 | 3 | 3 | 3 | 2 | 0 | 0 | 3 |   | 3 | 2 | 1 | 3 |
|   | 63  | 2 | 3 | 3 | 3 | 2 | 0 | 0 | 3 |   | 3 | 0 | 1 | 2 |
| C | 200 | 0 | 3 | 3 | 3 | 0 | 0 | 0 |   |   |   | 2 | 2 | 3 |
|   | 100 | 0 | 3 | 3 | 3 | 0 | 0 | 0 |   |   |   | 0 | 1 | 3 |
|   | 50  | 0 | 2 | 3 | 1 | 0 | 0 | 0 |   |   |   | 0 | 0 | 3 |
| D | 500 | 2 | 3 | 3 | 3 | 3 | 2 | 3 | 3 | 2 | 3 | 3 | 2 | 3 |
|   | 250 | 2 | 3 | 3 | 3 | 2 | 2 | 2 | 2 | 1 | 3 | 2 | 1 | 2 |
|   | 125 | 2 | 2 | 3 | 3 | 2 | 2 | 1 |   |   |   | 2 | 2 | 2 |
|   | 63  | 2 | 2 | 3 | 2 | 2 | 2 | 1 | 1 | 2 | 3 | 2 | 2 | 2 |
|   | 31  | 2 | 2 | 1 | 2 | 1 | 1 | 2 | 1 | 1 | 1 | 1 | 2 | 2 |
|   | 15  | 3 | 1 | 2 | 2 | 3 | 2 | 2 | 1 | 1 | 2 | 2 | 2 | 2 |

As shown above, the new compounds have excellent miticidal, ovicidal and insecticidal activity. The analogs of the compounds of Examples 2–4 which carry two bromine substituents are somewhat more active than the dichloro compounds shown above; the corresponding difluoro compounds are about equal in activity with the above shown compounds.

The compounds of the current invention may be applied in the form of emulsifiable concentrates, powders, granules or dusts. An agronomically acceptable carrier for the purposes of this invention includes any substance which can be used to dissolve, disperse or diffuse the above novel compounds, without impairing the effectiveness of the active ingredient, and which is not deleterious to the soil or the plant in any chemical or physical manner. Particularly favored compositions are those wherein the active ingredient is present in a range from 1–20% by weight and the mixture of active compound I and the diluent form a water-emulsifyable concentrate or it is a wettable powder. Diluents of this nature are well known in the agricultural formulation art. They include water containing a wetting agent or dispersant, or solid carriers such as diatomaceous earth, bentonite, etc.

In formulating the compositions of this invention, other components may be included to aid in the adsorption or absorption of the active ingredients by the plant. Components such as wetting agents, solubilizers, emulsifiers, humiditants, surfactants and other adjuvants useful for this purpose may be incorporated in the formulations.

The above compounds are preferably compounded with inert diluents to a liquid or solid composition containing between 10,000 and 200,000 ppm, particularly compositions containing 25,000 to 50,000 ppm. Such stock mixes are easily packaged and stable and can be diluted by the consumer to the necessary concentration for application in the field, i.e., to concentrations of between 500 to 2,500 ppm.

I claim:

1. A compound of the formula

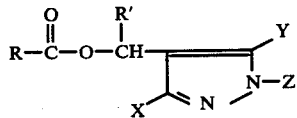

wherein R is phenyl, benzyl, 1-isopropylbenzyl wherein each of said aromatic rings may carry a chlorine substituent,

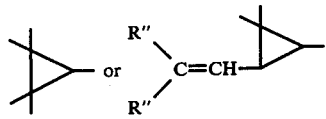

R' is H, —C≡N or —C≡CH;
R'' is chlorine, bromine, fluorine or methyl; X and Y both but independently are H or loweralkyl; and and Z is phenyl or benzyl which may carry an optional aromatic chlorine substituent.

2. The compound of claim 1 wherein X and Y are H, R' is C≡N, R is tetramethylcyclopropyl and Z is benzyl.

3. The compound of claim 1 wherein R is 2,2-dimethyl-3-(2,2-dimethylethenyl)-cyclopropyl, X and Y are H and Z is benzyl.

4. The compound of claim 1 wherein R is 2,2-dimethyl-3-(2,2-dichloroethenyl)cyclopropyl, X and Y are H, Z in benzyl and R' is ethynyl.

5. The compound of claim 1 wherein R is 1-p-chlorophenyl-2-methylpropyl, X and Y are H and Z is benzyl.

6. The compound of claim 5 wherein R' is H.
7. The compound of claim 5 wherein R' is C≡CH.
8. The compound of claim 5 wherein R' is C≡N.

9. An agronomically acceptable composition for controlling mites, insects or their eggs, containing as the active ingredient, between 1 and 20% by weight of a compound of the formula

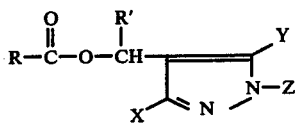

wherein R is phenyl, benzyl, 1-isopropylbenzyl wherein each of said aromatic rings may carry a chlorine substituent,

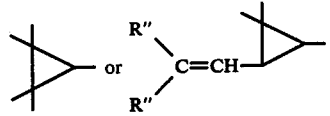

R' is H, —C≡N or —C≡CH;
R'' is chlorine, bromine, fluorine or methyl; X and Y both but independently are H or loweralkyl; and and Z is phenyl or benzyl which may carry an optional aromatic chlorine substituent, and an agronomically acceptable carrier.

10. The composition of claim 9 wherein X and Y are H, R' is C N, R is tetramethylcyclopropyl and Z is benzyl.

11. The composition of claim 9 wherein X and Y are H and Z is benzyl.

12. The composition of claim 9 wherein R is 2,2-dimethyl-3-(2,2-dichloroethenyl)cyclopropyl, X and Y are H, Z is benzyl and R' is ethynyl.

13. The composition of claim 9 wherein R is 1-p-chlorophenyl-2-methylpropyl, X and Y are H and Z is benzyl.

14. The composition of claim 9 wherein R' is H.
15. The composition of claim 14 wherein R is H.
16. The composition of claim 14 wherein R is C≡CH.
17. The composition of claim 14 wherein R is C≡N.